United States Patent [19]

Murphy et al.

[11] Patent Number: 5,300,632
[45] Date of Patent: Apr. 5, 1994

[54] **METHOD FOR PURIFYING AN OUTER MEMBRANE PROTEIN OF *HAEMOPHILUS INFLUENZAE***

[75] Inventors: Timothy F. Murphy, East Amherst; Michael A. Apicella, Pendleton, both of N.Y.

[73] Assignee: Research Foundation of State University of New York, Albany, N.Y.

[21] Appl. No.: 807,049

[22] Filed: Dec. 12, 1991

Related U.S. Application Data

[63] Continuation-in-part of Ser. No. 330,229, Mar. 29, 1989, abandoned, which is a continuation-in-part of Ser. No. 92,948, Oct. 8, 1987, Pat. No. 5,173,294, and a continuation-in-part of Ser. No. 932,872, Nov. 18, 1986, abandoned.

[51] Int. Cl.$^5$ .............................. C07K 3/24; A23J 3/20
[52] U.S. Cl. .................................... 530/420; 530/412; 530/418; 530/419; 530/427; 530/350; 530/825; 435/68.1; 435/891
[58] Field of Search ............... 530/350, 412, 418, 419, 530/420, 427, 825; 435/276, 891, 267, 270, 272, 68.1

[56] References Cited

U.S. PATENT DOCUMENTS

| | | | |
|---|---|---|---|
| 4,271,147 | 6/1981 | Helting et al. | 424/92 |
| 4,427,782 | 1/1984 | Caldwell et al. | 436/542 |
| 4,459,286 | 7/1984 | Hilleman et al. | 424/87 |
| 4,474,758 | 10/1984 | Kuo et al. | 424/92 |

FOREIGN PATENT DOCUMENTS

WO88/04932 7/1988 PCT Int'l Appl.
WO90/02557 3/1990 PCT Int'l Appl.

OTHER PUBLICATIONS

Munson, Jr. et al., "Purification and Partial Characterization of Outer Membrane Proteins P5 and P6 from *Haemophilus influenzae* Type b", *Infection and Immunity*, vol. 49, No. 3, 544-549, Sep., 1985.

Murphy et al., "Identification of a 16,600-Dalton Outer Membrane Protein on Nontypeable *Haemophilus influenzae* as a Target for Human Bactericidal Antibody", *The Amer. Soc. for Clin. Inv.*, vol. 78 1020-1027, Oct. 1986.

*Primary Examiner*—Michael G. Wityshyn
*Assistant Examiner*—C. Sayala
*Attorney, Agent, or Firm*—Nixon Hargrave Devans & Doyle

[57] ABSTRACT

The present invention provides a method for purification of a surface exposed, immunogenic outer membrane protein of *Haemophilus influenzas* which is conserved amongst strains. The protein, designated P6, is relatively free of detergent, contaminating RNA and undesirable cellular components.

In accordance with the present invention, there is provided a method for purifying an immunogenic outer membrane protein of *H. influenzas* consisting essentially of:

a) suspending *H. influenzas* micro-organisms by incubating the organisms in a detergent buffer to form an insoluble fraction comprising the outer membrane protein and peptidoglycan component and a soluble fraction comprising the remainder of the cellular components;

b) separating the insoluble fraction from the soluble fraction;

c) suspending the insoluble fraction in detergent buffer containing RNase and allowing for RNA digestion;

d) separating the insoluble fraction from the soluble fraction comprising the RNase and digested RNA;

e) solubilizing the insoluble fraction by heat-treating in a detergent-free buffer; and f) separating the soluble fraction containing the purified outer membrane protein from the insoluble fraction containing the peptidoglycan component.

15 Claims, 11 Drawing Sheets

Purification of P6: Approximate yields

P6 obtained from ~25 grams (wet weight) of bacterial cells:

Old Method
Murphy et al
< 1 mg (estimated from many batches)

New Method
Present Invention

| Batch | P6 |
|-------|------|
| MSD-A | 6.3 mg |
| MSD-B | 8.0 mg |
| MSD-C | 9.5 mg |
| MSD-D | 11.2 mg |
| MSD-E | 12.2 mg |
| MSD-F | 17.0 mg |
| MSD-G | 9.5 mg |
| MSD-H | 9.9 mg |

Fig. 10.

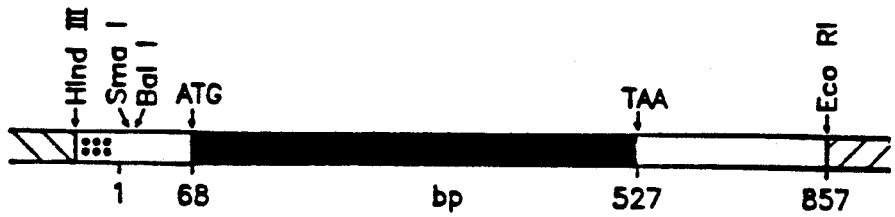

Fig. 11(a).

CCCAAGTAAAATTTCCAGCTTGGTCTCCATACTTAACTAAATAAAAAACTCATTTAGGAGAAATCTA
1                                                              ==== met asn lys phe val lys ser leu leu val ala gly ser val ala ala leu
ATG AAC AAA TTT GTT AAA TCA TTA TTA GTT GCA GGT TCT GTA GCT GCA TTA
68                                                  100 ala ala cys ser ser ser asn asn asp ala ala gly asn gly ala ala gln
GCG GCT TGT AGT TCC TCT AAC AAC GAT GCT GCA GGC AAT GGT GCT GCT CAA thr phe gly gly tyr ser val ala asp leu gln gln arg tyr asn thr val
ACT TTT GGC GGA TAC TCT GTT GCT GAT CTT CAA CAA CGT TAC AAC ACC GTA
                                            200 tyr phe gly phe asp lys tyr asp ile thr gly glu tyr val gln ile leu
TAT TTT GGT TTT GAT AAA TAC GAC ATC ACC GGT GAA TAC GTT CAA ATC TTA asp ala his ala ala tyr leu asn ala thr pro ala ala lys val leu val
GAT GCG CAC GCA GCA TAT TTA AAT GCA ACG CCA GCT GCT AAA GTA TTA GTA
                                    300 glu gly asn thr asp glu arg gly thr pro glu tyr asn ile ala leu gly
GAA GGT AAT ACT GAT GAA CGT GGT ACA CCA GAA TAC AAC ATC GCA TTA GGA gln arg arg ala asp ala val lys gly tyr leu ala gly lys gly val asp
CAA CGT CGT GCA GAT GCA GTT AAA GGT TAT TTA GCA GGT AAA GGT GTT GAT
                                400 ala gly lys leu gly thr val ser tyr gly glu glu lys pro ala val leu
GCT GGT AAA TTA GGC ACA GTA TCT TAC GGT GAA GAA AAA CCT GCA GTA TTA gly his asp glu ala ala tyr ser lys asn arg arg ala val leu ala tyr
GGT CAC GAT GAA GCT GCA TAT TCT AAA AAC CGT CGT GCA GTG TTA GCG TAC
                                500 termination
TAA TTCTTGGTATTTCTAATACTTGAAAAACAGGATCCATTTTTTATTGGATCCTGTTTTGTTTTC

ATCGTTTGTAATTTAACCAATTAGCTTGAAAGAATGAATTTATTCTTTTGATTCTAAAATAAATGCG
            600
TTATCATTAACTCATCAACACAGTGGGTCGTTAGCTCAGTCGGTAGAGCAGCGGACTTTTAATCCGT
                                    700
TGGTCGAAGGTTCGAATCCTTCACGACCCACCACTCTCTGATTTAATTGTCCAGTTGGGTTGTTAGC

TCAGTTGGTAGAGCAGCGGACTCTTAATTCGTCGGTCGAGAGTTCGAGCCTCTCACAACCTACCATT
        800
CTTACCG

Fig. 11(b).

METHOD FOR PURIFYING AN OUTER MEMBRANE PROTEIN OF HAEMOPHILUS INFLUENZAE

This application is a continuation-in-part of U.S. Ser. No. 330,229 filed Mar. 29, 1989, now abandoned, which is a continuation-in-part of U.S. Ser. No. 092,948, now U.S. Pat. No. 5,173,294 filed Oct. 8, 1987 and U.S. Ser. No. 932,872 filed Nov. 18, 1986, abandoned.

BACKGROUND OF THE INVENTION

Haemophilus influenzas type b has long been recognized as a frequent pathogen, particularly in infants and children. Only recently has nontypeable H. influenzas been recognized as an important pathogen. It is now well established that nontypeable H. influenzas causes pneumonia, bacteremia, meningitis, postpartum sepsis and acute febrile tracheobronchitis in adults. In addition, nontypeable H. influenzas causes neonatal sepsis and is a frequent etiologic agent in acute otitis media in infants and children. The importance of discovering a method to assay a clinical sample such as sputum, cerebral spinal fluid, blood and others for the presence of H. influenzas is evident.

The recent observation that nontypeable H. influenzae causes serious infections in adults and children has stimulated interest in study of the pathogenesis and potential virulence factors associated with this bacterium. It has been shown that the ribitol capsule of H. influenzas type b is a virulence factor for the organism. Thus, antibody to the capsule protects the host by means of bactericidal and/or opsonizing actions. These observations have generated much investigation on the role of the capsular polysaccharide in infection with H. influenzas type b and protection from these infections. However, nontypeable H. influenzas lacks a polysaccharide capsule. Similar to the outer membranes of other gram-negative bacteria, the outer membrane of H. influenzas is composed of outer membrane proteins (OMPS) and lipooligosaccharides (LOS). Thus, studies of the relationship between virulence of nontypeable H. influenzas and surface antigens focus on OMPs and LOS.

Analysis of OMPs of nontypeable H. influenzas has shown that there are marked differences in OMP composition amongst strains. For example reference is made to Murphy et al, A Subtyping System For Nontypeable Haemophilus influenzae Based on Outer-membrane Proteins, J. Infect. Dis, 1983, 147:838–46; Barenkamp et al, Outer Membrane Protein and Biotype Analysis of Pathogenic Nontypeable Haemophilus influenzas, Infect. immun, 1982, 36:535–40; Lorb et al, Outer Membrane Protein Composition in Disease Isolates of Haemophilus influenzas, Pathogenic and Epidemiological Implications, Infect. Immun., 1980, 30:709–17.

A subtyping system for nontypeable H. influenzas based on the major OMPs has previously been developed. However, a surface exposed antigen (immunogen) which is conserved amongst strains would be an important tool in developing a method of identifying H. influenzas in clinical specimens as well as a vaccine against H. influenzas. Furthermore, there is a need for a new and improved method for purifying the surface enposed antigen.

U.S. Pat. No. 4,427,782 Caldwell et al., discloses purification of the outer membrane protein of Chlamydia trachomatis. The prior art method described by Caldwell et al is outlined in the flow chart as shown in FIG. 1. However, this method calls for collecting the supernatant from which the OMP of C. trachomatis is isolated. This method is not applicable to the isolation of the outer membrane protein of H. influenzas because following the teaching of Caldwell one would discard the OMP of H. influenzas in the supernatant.

The prior art method of Murphy et al., J. Clin. Invest., 1986, 78:1020, discloses an improvement over the method of Munson and Granoff, Infect. Immun., 1985, 49:544–549, for isolation of the outer membrane protein, P6, of Haemophilus influenzas. The method described by Murphy et al is outlined in the flow chart as shown in FIG. 2. The initial steps of this purification method include preparation of an outer membrane complex consisting of outer membrane protein, peptidoglycan and LOS by sequential incubation of the bacteria in a detergent such as sarcosyl. But, this method tends to be time consuming as well as yielding little product, less than about 1 mg from about 25 grams (wet weight) of bacterial cells. Furthermore, the Murphy et al method teaches the use of a final buffer which contains a detergent such as SDS. The resultant purified product, P6, contains detergent such as SDS, possibly residual sarcosyl contamination RNA and undesirable cellular component. Consequently, the usefulness of the purified protein in subsequent applications such as vaccine preparation is limited because detergents (SDS) are not allowed in vaccine formulations.

OBJECTS AND SUMMARY OF THE INVENTION

Therefore, the primary object of the present invention is to provide a method for purification of a surface exposed antigen of H. influenzas which is conserved amongst strains.

Another object of the present invention, is to provide such a purification method which will produce a product free of detergent, contaminating RNA and undesirable cellular components.

Another object of the present invention, is to provide such a purification method which is relatively simple and produces an increased yield of the desired antigen.

In accordance with the present invention, there is provided a method for purifying an immunogenic outer membrane protein of H. influenzas comprising:
  a) suspending H. influenzas micro-organisms by incubating the organisms in a detergent buffer to form an insoluble fraction comprising the outer membrane protein and peptidoglycan component and a soluble fraction comprising the remainder of the cellular components;
  b) separating the insoluble fraction of step a) from the soluble fraction;
  C) suspending the insoluble fraction of step b) in detergent buffer containing RNase and allowing for RNA digestion;
  d) separating the insoluble fraction of step c) from the soluble fraction comprising the RNase and digested RNA;
  e) solubilizing the insoluble fraction of step d) by heat-treating in a detergent-free buffer; and
  f) separating the soluble fraction containing the purified outer membrane protein from the insoluble fraction of step e) containing the peptidoglycan component.

BRIEF DESCRIPTION OF THE DRAWING FIGURES

FIG. 1 is a flowchart illustrating the purification method as disclosed by Caldwell et al in U.S. Pat. No.4,427,782;

FIG. 2 is a flowchart illustrating the purification method as disclosed by Murphy et al, *J. Clin. Invest.,* 1986, 78:1020;

Figure 1:
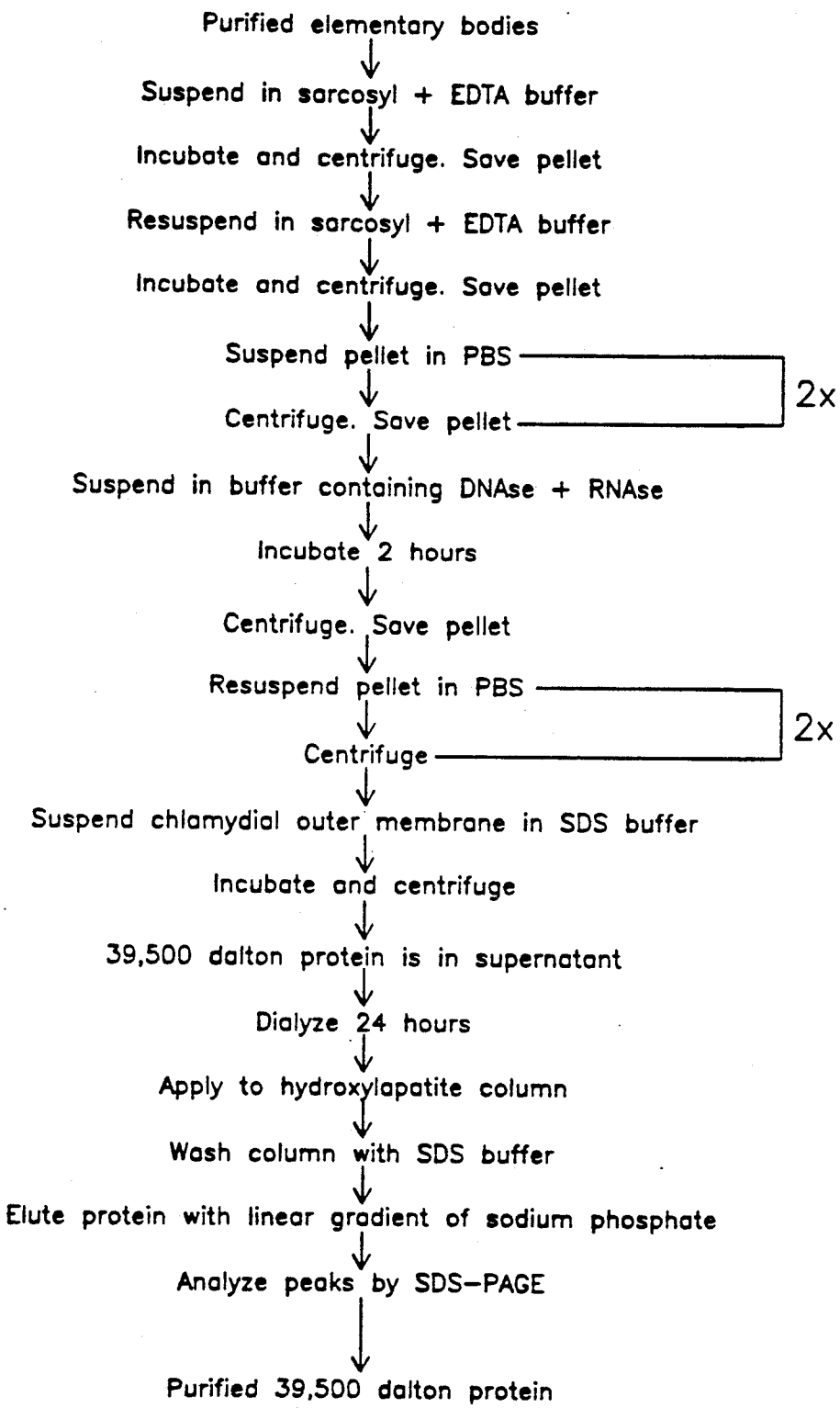

FIG. 10 is a table showing the comparison of approximate yields of P6 obtained from about 25 grams (wet weight) of bacterial cells using the method of Murphy et al, *J. Clin. Invest.,* 1986, 78:1020, and the method of the present invention;

FIG. 11(a) shows a restriction map of the gene of the present invention;

FIG. 11(b) shows the DNA sequence and corresponding amino acid sequence of the gene of the present invention.

DETAILED DESCRIPTION OF THE INVENTION

As used herein, the term "nontypeable *H. influenzae*" means *H. influenzas* which lacks a polysaccharide capsule and wherein the outer membrane comprises outer membrane proteins (OMPS) and lipooligosaccharides (LOS).

As used herein, "immunogenic portion" means that portion which will result in an immunological antibody response in a host organism. The "immunogenic portion" may be an antigen.

As used herein, "epitope" means that limited immunogenic portion which results in a specific immunological response.

As used herein, "P6" is an outer membrane protein having a molecular weight of about 15,000 to about 17,000 daltons, and initially about 16,000 to about 16,600 daltons. As used herein, "R Nase" refers to "ribonuclease".

In accordance with the present invention, a mouse monoclonal antibody which recognizes an epitope on an approximately 16,000 dalton outer membrane protein (hereinafter designated P6) was developed to nontypeable *H. influenzas*. This epitope was present i.e., conserved, on all 115 isolates of *H. influenzas* tested, including typeable and nontypeable strains. Screening of 89 strains of other bacteria demonstrated that this epitope is a highly specific marker for *H. influenzas* because the epitope was absent in virtually all other bacterial species tested. Western blot assays were performed with two normal human serum samples and convalescent-phase serum from an adult with bacteremia due to nontypeable *H. influenzas*. Antibody to the 16,000 dalton outer membrane protein was present in all three human serum samples.

Prototype strains of nontypeable *H. influenzas* representing the eight outer membrane protein subtypes were obtained from the inventors own collection, Murphy et al, Erie County Medical Center and Buffalo V. A. Medical Center, Buffalo, N.Y. Strain 3524 was isolated from the sputum of a patient with chronic bronchitis at the Erie County Medical Center, Buffalo, NY. 14 strains of nontypeable *H. influenzas* from blood or transtracheal aspirates were provided by Dr. S. Berk, V. A. Medical Center, Mountain Home, Tenn. The remaining strains of nontypeable *H. influenzas* were clinical isolates from the Erie County Medical Center and Buffalo V. A. Medical Center, Buffalo, N.Y. 54 strains of *H. influenzas* type b were provided by Dr. J. Ward, University of California at Los Angeles. The remaining strains of *H. influenzas* type b were clinical isolates from Buffalo Children's Hospital, Buffalo, N.Y. Reference strains of other capsular serotypes of *H. influenzas* as used herein, were obtained from the Centers for Disease Control in Atlanta, Ga.

Copies of *H. paraphrophilus* A.T.C.C. 29240, H. segnis A.T.C.C. 10977, *H. parainfluenzae* A.T.C.C. 7901 and 9276, *H. aegypticus* A.T.C.C. 11116, *H. parahemolyticus* A.T.C.C. 10014, nontypeable *H. influenzas* A.T.C.C. 19418, *Actinobacillus actinomycetemcomitans* A.T.C.C. 29522, A.T.C.C. 29523, A.T.C.C. 29524, N.C.T.C. 9707, and N.C.T.C. 9110, *A. eguili* A.T.C.C. 19392, *A. seminis* A.T.C.C. 15768, and *A. suis* A.T.C.C. 15557 were provided by Dr. J. Zambon, School of Dentistry, State University of New York at Buffalo, Buffalo, N.Y. Isolates of all other species were provided by the clinical microbiology laboratory at the Erie County Medical Center.

The identity of strains of *H. influenzas* was confirmed by colonial morphology and growth requirement for hemin and nicotinamide adenine dinucleotide (AND). Capsular serotypes were determined by CIE with use of reference strains and antiserum from the Centers for Disease Control. Strains were stored in Mueller-Hinton broth plus 10% glycerol at −70° C.

BALB/c mice were immunized i.p. with 0.1 ml of 109 cells of nontypeable *H. influenzas* strain 3524 on days 0 and 28. On day 32 after initial immunization, selected animals were killed with chloroform, their spleens removed and splenic lymphocytes harvested by perfusion of splenic pulp with minimal essential medium (MEM).

To achieve hybridoma development by fusion of donor spleen cells to NS 1 (nonsecreting variant of the IgG1 BALB/C plasmacytoma P3XAg8) plasmacytoma cells, (obtained from the Salk Institute of Biology, La Jolla, Ca., under National Cancer Institute contract N01-CB-23886) 35% polyethylene glycol was used in a modification of the procedure of Kennett, Cell Fusion, *Methods Enzymol,* 1979, 58:345–359, the disclosure of which is hereby incorporated by reference. That is, $10^7$ spleen cells were combined with $10^6$ NS-1 cells in minimal essential medium with serum. The cells were centrifuged at 170 xg for 10 minutes at 25° C. The supernatant was removed and the pellet loosened by tapping. Two-tenths milliliter of 35% polyethylene glycol 1,000 (Sigma Chemical Co., St. Louis) in minimal essential medium (MEM) without serum was added. The mixture was stirred gently and left at 25° C. for 8 minutes, with the last 3 minutes consisting of centrifugation at 500 xg to pellet the cells. At the end of the original 8 minutes, 5 ml of minimal essential medium (MEM) with serum was added and gently pipetted once to resuspend the pellet. The mixture was centrifuged at 250 xg for 5 minutes at 25° C. (room temperature), and all of the supernatant was removed. Five milliliters of complete minimal essential medium (medium with glucose [4.5 mg/ml] and 20% fetal bovine serum) was added to resuspend the pellet. The mixture was transferred to a 25 ml Erlenmyer flask containing the appropriate amount of complete minimal essential medium to obtain $3 \times 10^5$ plasmacytoma cells/ml. The cells were stirred gently and distributed into microtiter wells in 0.05 ml samples.

At 24 hours after polyethylene glycol fusion, 0.05 ml of medium containing hypoxanthine (13.6 μg/ml), aminopterin (0.36 μg/ml), and thymidine (3.87 μ/ml) was added to each well. The microtiter plates were placed in a tissue culture incubator at 85% humidity in an atmosphere of 5% $CO_2$ and 95% room air. Fresh medium containing hypoxanthine, aminopterin, and thymidine was added on day 7, and plates were checked for macroscopic plaques after day 10. The supernatant from all wells was tested for the presence of antibody with an enzyme linked immunosorbent assay (ELISA). ELISAs were performed in polyvinyl 96 well microtiter plates (Dynatech, Alexandria, Va.). 200 μl volumes were used for each step. Wells were coated with a cell envelope preparation (10 μg/ml) of nontypeable *H. influenzas* strain 3524 prepared according to the method of Johnston, Immunobiology of *Neisseria gonorrhoeae*, *American Society for Microbiology*, 1978, 121-9, the disclosure of which is hereby incorporated by reference. Plates were incubated at 37° C. for 1 hour followed by overnight incubation at 4° C. Wells were washed three times with phosphate buffered saline (PBS) plus 0.05% Tween 20[R] surfactant between each step. Unbound sites on the plastic were blocked with 3% bovine serum albumin in PBS for 2 hours at 37° C. Tissue culture supernatants (or dilutions of mouse ascites fluid in subsequent experiments) containing monoclonal antibody were incubated in the wells overnight at 4° C. Rabbit antibody to mouse IgG and IgM was then incubated for 2 hours at 37° C. followed by protein A-peroxidase for 2 hours at 37° C. 200 μl of substrate was then added to each well. Substrate was prepared by dissolving 10 mg of o-phenylenediamine in 1 ml of methanol and adding this solution to 99 ml of citrate-phosphate buffer, pH 5.0, plus 0.1 ml of 3% $H_2O_2$. After the substrate was incubated for 45 minutes in the dark at 25° C. (room temperature), the reaction was stopped with 50 μl of 4 N $H_2SO_4$ and the $OD_{490}$ was measured. Each set of ELISAs was performed with a control in which NS-1 tissue culture supernatant or ascites fluid was used in place of the monoclonal antibody being tested. On the basis of the results of ELISA screening, selected clones were propagated by subsequent transfer to larger tissue culture wells. Large quantities of antibody were produced in tissue culture and by i.p. injection of $10^5$ hybridoma cells into pristane-primed BALB/C mice. The resulting ascitic fluid was harvested in three to four weeks and tested for specificity.

The strains to be assayed were grown on chocolate agar, or other appropriate medium depending on the species, overnight at 37° C. in an atmosphere of 95% room air and 5% $CO_2$. Cells from one plate were harvested by suspension in PBS and centrifugation at 10,000 xg for 20 minutes. The resulting pellet was suspended in enough PBS to allow the suspension to be drawn into a micropipette. 1/10 ml of the suspension of bacteria was added to 0.4 ml of sample buffer (0.06 M Tris, 1.2% SDS, 1% B-mercaptoethanol, and 11.9% glycerol) and heated for 5 minutes in a boiling water bath. The resulting organisms are referred to as whole cell preparation.

A 10 μl drop of whole cell preparation was placed on a nitrocellulose sheet (Schleicher and Schuell, Inc., Keene, N.H.) and allowed to air-dry. Then, the sheet was placed in 3% gelatin in Buffer A (0.012 M Tris and 0.15 M NaCl, pH 7.4) for 1 hour. After the sheet was rinsed with Buffer A, it was placed in an appropriate dilution of antibody and allowed to shake at room temperature (25° C.) overnight. The sheet was rinsed with Buffer A and placed in 1:3,000 dilution of protein A peroxidase (Zymed Laboratories, San Francisco) and shaken for 1 hour at 25° C. The sheet was rinsed and immersed in horseradish peroxidase color development solution (0.015% $H_2O_2$; Bio-Rad, Richmond, Calif.) for 45 minutes. Controls assayed on each sheet included sample buffer as a negative control. A negative result was recorded when the dot was no different from the background color, and a positive result was recorded when the dot turned purple-blue. About 90% of dot assays were unequivocally positive or negative. Those strains that yielded equivocal results in the dot assay were subjected to Western blot assay.

EXAMPLE I

Preparation of LOS

Lipooligosaccharide (LOS) was prepared from nontypeable *H. influenzas* strain 3524 by two methods. The first method was a modification of the phenol-water extraction method described by Westphal et al, Bacterial Lipopolysaccharides, *Methods in Carbohydrate Chemistry*, 1965, 5:83-91, the disclosure of which is hereby incorporated by reference. The second method was that described by Hitchcock and Brown, *Journal of Bacteriology*, 1983, 154:269-77, the disclosure of which is hereby incorporated by reference. The latter method uses the enzyme proteinase K (Boehringer Mannheim GmbH, Mannheim, Federal Republic of Germany), which hydrolyzes proteins but has no effect on LOS.

Whole cell and LOS preparations were subjected to sodium dodecyl sulfate polyacrylamide gel electrophoresis (SDS-PAGE) with either 11% or 13.2% separating gels, as described by Murphy et al, *J. Clin. Invest.*, 1986, 78:1020, the disclosure of which is hereby incorporated by reference. When electrophoresis was complete, the gel was placed with a nitrocellulose sheet that had been previously boiled in distilled water. The sheet was immersed in 0.3 M sodium citrate plus 3 M NaCl. Electrophoretic transfer was carried out in a TransBlot[R] cell (Bio-Rad) at 50 V for 90 minutes. The electrode buffer was 0.025 M Tris, pH 8.3, 0.192 M glycine and 20% methanol. The nitrocellulose sheet was then treated exactly as described for the dot assay. That is, it was blocked with 3% gelatin and incubated sequentially with antibody 7F3, protein A-peroxidase and substrate horseradish peroxidase color developer.

EXAMPLE II 125I-radiolabeling of surface OMPS.

Figure 3:
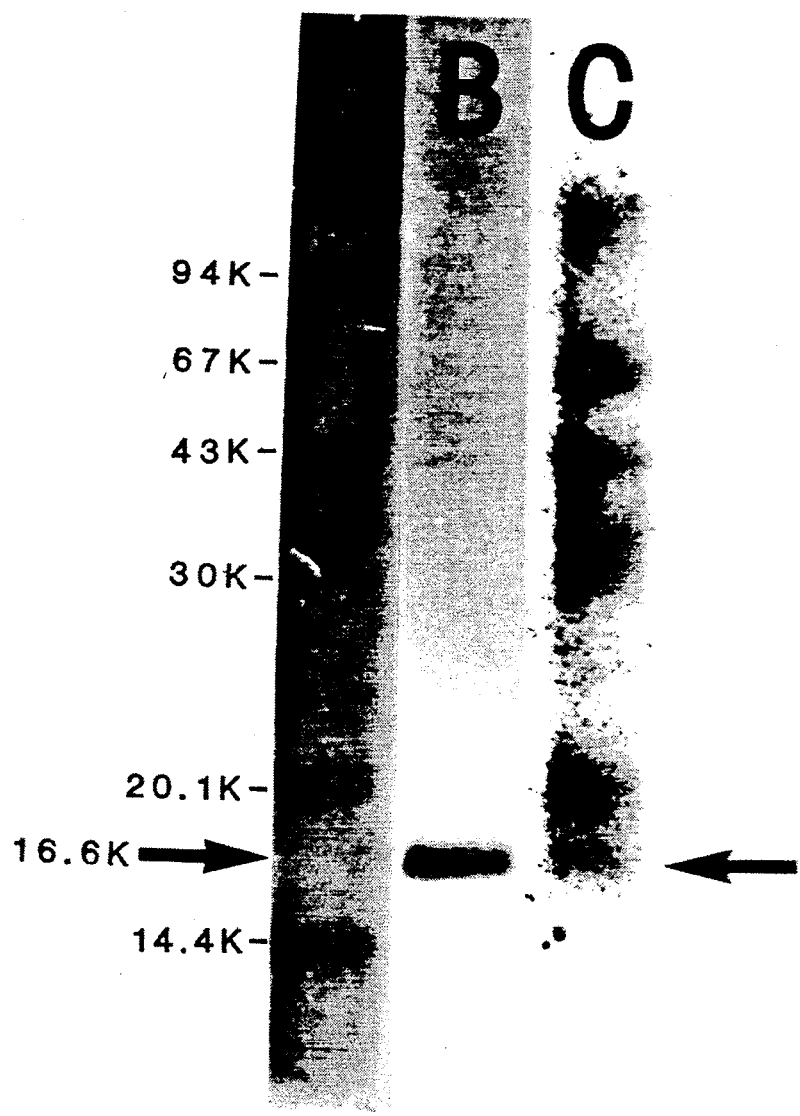
FIG. 3 is a photograph showing a Western Blot assay characterizing the OMP recognized by 7F3.

Extrinsic labeling of surface-exposed outer membrane proteins was accomplished using the lactopero,- idase catalyzed radioiodination procedure as described by Hansen et al, Infect. Immun. 1981, 32:1084-92, the disclosure of which is hereby incorporated by reference. The ELISA with outer membranes of nontypeable *H. influenzas* strain 3524 coated on microtiter plates demonstrated that hybridoma designated 7F3 was producing antibody 7F3 that recognized a determinant in the outer membrane of the bacterium. Gel immunodiffusion indicated that this antibody was of the IgG3 isotype. With reference to FIG. 3, there is illustrated a photograph of a Western blot assay which shows that the determinant recognized by antibody 7F3 was on a protein with a molecular size of approximately 16,600 daltons. Lane A (FIG. 3) shows the molecular weight standards on the nitrocellulose sheet transferred from a 13.2% gel. Lane B (FIG. 3) shows the approximate 16,600 dalton protein recognized by antibody 7F3 in a whole cell preparation of nontypeable H. influenzas strain 3524 incubated with antibody 7F3, protein A-peroxidase, and peroxide substrate. Lane C (FIG. 3) is an autoradiograph of a whole cell preparation of nontypeable *H. influenzas* strain 3524 made from bacteria extrinsically labeled with $^{125}I$. All three lanes were from the same gel. Western blot assay conducted as described above on 25 strains of *H. influenzas* showed that antibody 7F3 recognized a determinant on this approximate 16,600 dalton protein in all 25 strains. Since the antibody recognized a determinant on a protein of identical molecular size in the multiple strains, a larger number of strains was screened using a dot assay.

To determine whether the protein recognized by antibody 7F3 could be extrinsically labeled, nontypeable H. influenzas strain 3524 was labeled with $^{125}I$. The proteins were subjected to SDS-PAGE and transferred to a nitrocellulose sheet. One lane was exposed to X-ray film and another lane incubated with 7F3, protein A-peroxidase conjugate and substrate. With reference to FIG. 3, it is evident that the band recognized by antibody 7F3 (lane B) corresponds to an $^{125}I$-labeled band (lane C).

Two additional experiments were conducted to determine whether the epitope recognized by antibody 7F3 was on a protein or an LOS. An ELISA was performed as described above in which some wells were coated with a cell envelope preparation of nontypeable *H. influenzas* strain 3524 and other wells were coated with LOS prepared from nontypeable *H. influenzas* strain 3524 by the phenol-water method described by Westphal et al, Bacterial Lipopolysaccharides, Methods in Carbohydrate Chemistry, 1965, 5:83-91, the disclosure of which is hereby incorporated by reference. Antibody 7F3 was reactive with a cell envelope preparation ($OD_{0.375}$) that contained OMPs and LOS but was nonreactive with LOS ($OD_{0.062}$). This indicates that the epitope recognized by antibody 7F3 resides on an OMP.

Figure 4:
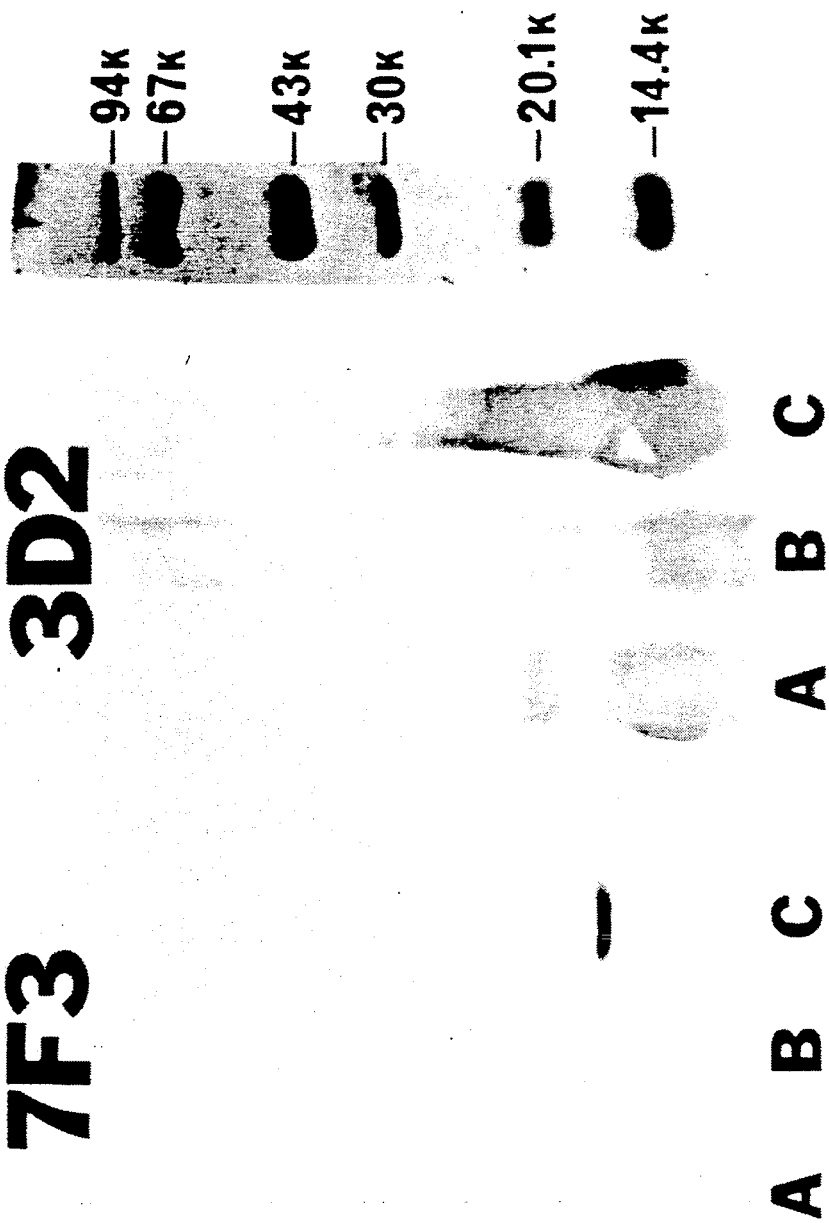
FIG. 4 is a photograph showing a Western Blot assay assesing whether the epitope recognized by antibody 7F3 is on the protein or LOS.

With reference to FIG. 4, there is shown a photograph of a Western blot assay depicting another experiment designed to assess whether the epitope recognized by antibody 7F3 is on a protein or LOS. The lanes marked A contain LOS prepared by proteinase K lysis of cells of strain 3524 as described by Hitchcock et al, *J. Bacterial,* 1983, 154:269-77, the disclosure of which is hereby incorporated by reference. The lanes marked B contain LOS of strain 3524 prepared by the phenol-water procedure of Westphal et al. as described elsewhere herein. The lanes marked C contain whole cell preparations of strain 3524. All samples were assayed on the same gel and transferred to the same nitrocellulose sheet. FIG. 4 (left) was incubated with antibody 7F3 (ascites fluid dilution 1:500). FIG. 4 (right) was incubated with antibody 3D2 (ascites fluid dilution 1:500), a monoclonal antibody which recognizes the lipid A portion of *H. influenzas* LOS. Antibody 7F3 only binds to a band with a molecular weight of approximately 16,600 in the whole cell preparation and does not bind to either of the LOS preparations. This observation further demonstrates that antibody 7F3 recognizes an epitope on a protein and not on LOS.

More specifically, FIG. 4 (left) shows a Western blot assay from a 13.2% gel incubation with antibody 7F3. FIG. 4 (right) shows incubation with antibody 3D2, which recognizes an epitope on the lipid A of *H. influenzas*. The lanes marked A contain LOS of nontypeable *H. influenzas* strain 3524 prepared by lysis of cells with proteinase K. The lanes marked B contain phenol-water prepared LOS of strain 3524. The lanes marked C contain whole cell preparations of strain 3524. Molecular weight standards are noted on the right side of the Figure.

Studies were conducted to determine the species specificity of the antigen recognized by antibody 7F3. Whole cell preparations of 115 isolates of *H. influenzas* were performed by either dot assay or Western blot assay. The strains included 73 type b, 37 nontypeable, and 1 each of types a and c-f. All 115 strains of *H. influenzas* contained the epitope recognized by antibody 7F3. This result indicates that this epitope is a common antigen amongst strains of *H. influenzas*.

Sixty isolates of various bacterial species were studied to determine whether this conserved epitope is present in bacteria other than *H. influenzas*. With reference to Table 1, all 60 of those strains studied lacked the determinant recognized by antibody 7F3.

TABLE 1

SPECIFICITY OF ANTIBODY 7F3 FOR VARIOUS BACTERIAL SPECIES

| Bacterium | No. Tested | No. Positive |
|---|---|---|
| Gram-negative | | |
| *Escherichia coli* | 10 | 0 |
| *Actinobacillus* species | 10 | 0 |
| *Proteus* species | 7 | 0 |
| *Pseudomonas* species | 5 | 0 |
| *Klebsiella* species | 4 | 0 |
| *Serratia* species | 4 | 0 |
| *Enterobacter cloacae* | 1 | 0 |
| *Morganella morganii* | 1 | 0 |
| *Neisseria gonorrhoeae* | 6 | 0 |
| *Neisseria* species | 2 | 0 |
| Gram-positive | | |
| *Staphylococcus aureus* | 5 | 0 |
| *Staphylococcus* species | 2 | 0 |
| *Viridans streptococci* | 1 | 0 |
| *Streptococcus faecalis* | 1 | 0 |
| Diphtheroids | 1 | 0 |
| Total | 60 | 0 |

Twenty-nine strains of Haemophilus species other than *H. influenzae* were studied. With reference to Table 2, twenty-five of these isolates lacked the 7F3 epitope. Two strains of *H. parahemolyticus* contained the determinant. In addition, one strain of *H. paraphrophilus* and one of *H. aegypticus* contained about a 20,000 dalton protein that was recognized by antibody 7F3.

TABLE 2
SPECIFICITY OF ANTIBODY 7F3 FOR VARIOUS SPECIES OF HAEMOPHILUS

| Species | No. Tested | No. Positive |
|---|---|---|
| H. parainfluenzae | 24 | 0 |
| H. parahemolyticus | 2 | 2 |
| H. paraphrophilus | 1 | 1* |
| H. segnis | 1 | 0 |
| H. aegypticus | 1 | 1* |
| Total | 29 | 4 |

*In the Wester blot assay, antibody 7F3 recognized about a 20,000 dalton protein in these strains.

EXAMPLE III

Human serum antibody

Figure 5:
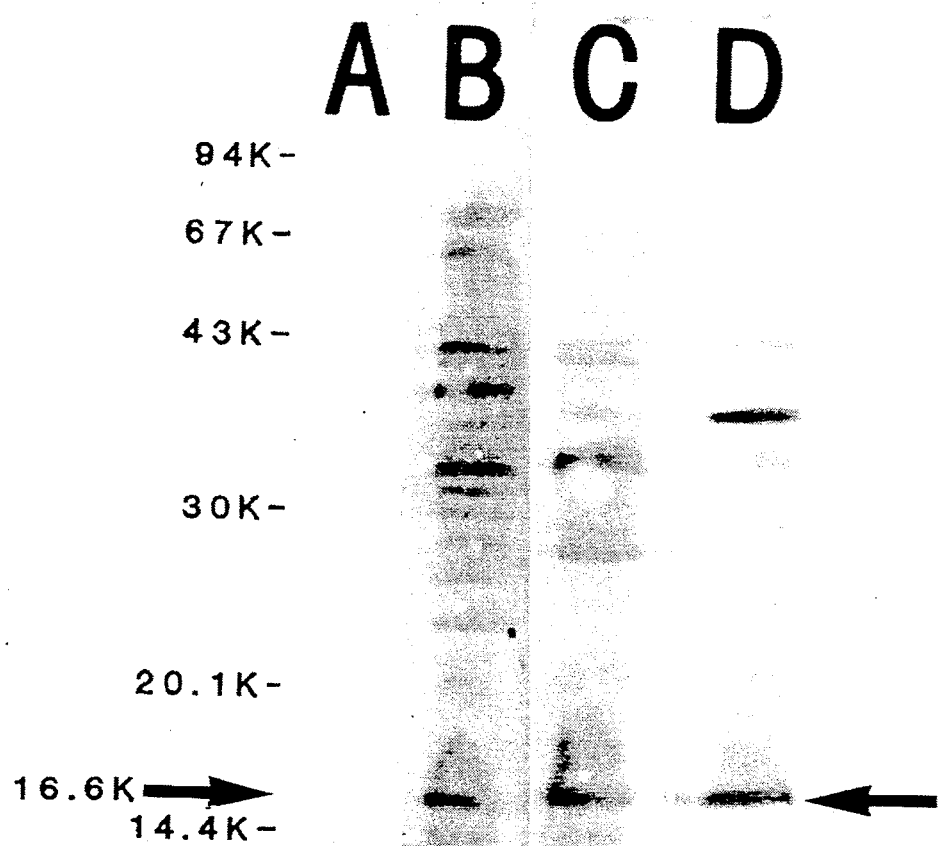
FIG. 5 is a photograph showing whole cell preparations of nontypeable *H. influenzas* strain 3524 assayed on the same gel and transferred to nitrocellulose paper.

Human serum was tested for the presence of antibody to the 16,600 dalton OMP by Western blot assay. With reference to FIG. 5, there are shown whole cell preparations of nontypeable H. influenzas strain 3524 that were assayed on the same gel and transferred to nitrocellulose paper. Lane A was incubated with 7F3 ascites fluid and shows a single band corresponding to the 16,600 dalton protein. Lanes B and C were incubated with two different samples of normal human serum, and lane D was incubated with serum obtained from an adult 17 days after the onset of bacteremia due to nontypeable H. influenzas. All three samples of human serum have antibody to the approximate 16,600 dalton OMP that contains the determinant recognized by antibody 7F3. It is worth noting that this band is among the most prominent recognized by antibody in human serum. With reference to FIG. 11(b), the DNA sequence for the gene expressing this 16,600 dalton outer membrane protein is believed to begin at nucleotide 125 and continue until nucleotide 526. The amino acid sequence deduced from the nucleotide sequence is also shown, wherein the amino terminus of the processed protein is depicted and believed to begin at amino acid 20 (cys) as also designated by corresponding nucleotide 125. With reference to Fig. 11(a), there is shown the restriction map of the gene.

Referring again to FIG. 5 in more detail, there is shown a Western blot assay from a 13.2% gel. All four lanes contain whole cell preparations of nontypeable H. influenzas strain 3524 from the same gel, however, each lane was incubated with a different antiserum: lane A antibody 7F3; lanes B and C two different samples of normal human serum (dilution, 1:500); and lane D serum obtained 17 days after the onset of bacteremia due to nontypeable H. influenzas in an adult (dilution 1:500). The incubation with antiserum was followed by incubation with protein A peroxidase and peroxide substrate. The arrows indicate that all three samples of human serum contain antibody to the approximate 16,600 dalton OMP that contains the 7F3 epitope. For references, molecular weight standards are indicated on the left.

In accordance with the invention, an IgG3 mouse monoclonal antibody that recognizes an epitope on an approximately 16,000 dalton OMP on the surface of nontypeable H. influenzas has been developed. This epitope is present in all 115 isolates of H. influenzas tested, including typeable and nontypeable strains. Screening of 60 strains of non-Haemophilus species demonstrated that the epitope is absent in all of these bacteria. The epitope was absent in 24 strains of H. parainfluenzae but was present in four to five strains of other Haemophilus species (Table 2). These species are unusual pathogens in humans and, therefore, from the standpoint of clinically relevant isolates, antibody 7F3 is highly specific for H. influenzas.

The monoclonal antibody of the present invention which recognizes a common epitope that is highly specific for H. influenzas can be useful as a diagnostic tool in clinical microbiology. A rapid test to confirm the identity of a clinical isolate as being H. influenzas (typeable or nontypeable) may be developed from such an antibody. In order to construct a DNA probe to exploit this specific epitope, the DNA sequence of the gene encoding P6 was determined. Once the DNA sequence was obtained, the amino acid sequence of the active P6 protein can be deduced. This information was then used to conduct epitope mapping. One way of epitope mapping involves the construction of a number of small peptides and, the subsequent testing of these peptides for reactivity with monoclonal antibody 7F3. Since the epitope recognized by 7F3 is specific for H. influenzas, the corresponding peptide recognized by that antibody represents the specific determinant on H. influenzas. Once the amino acid sequence of the peptide is known, the DNA sequence of that segment can be deduced. Since H. influenzas contains the gene which codes for this epitope, the bacterium is known to contain DNA which has a sequence corresponding to this sequence. A DNA probe can, therefore, be constructed to correspond to the nucleic acids which code for the specific epitope on P6. Once the probe is constructed, it can be labeled, for example, with a radioactive member. This probe can then be used to assay a clinical sample such as sputum, cerebral spinal fluid, blood and others for the presence of H. influenzas. The probe will bind to its complementary base pairs which are present in the genome of H. influenzas. This probe, once constructed, would represent an advantage over the current method of demonstrating growth requirements for hemin and nicotinamide adenine dinucleotide. Furthermore, an assay with a specific monoclonal antibody would yield results 24 hours earlier.

OMPs and LOS are closely associated on the outer membranes of gram-negative bacteria. This factor and the observation that the determinant recognized by antibody 7F3 is in the molecular weight range where LOS separates, leads one to question whether this determinant is on a protein or an LOS. Several lines of evidence indicate that the epitope recognized by antibody 7F3 is on a protein. First, staining with Coomassie blue on SDS gels demonstrated the presence of a band recognized by antibody 7F3 at approximately 16,000 daltons in all strains of H. influenzas. Because Coomassie blue stains protein but not LOS, this observation is presumptive evidence that antibody 7F3 recognizes a protein determinant. Second, the configuration of the band on SDS-PAGE and Western blot was typical for protein. The LOS showed multiple bands that were generally less distinct than the band at which the antibody 7F3 epitope resides. The monoclonal antibodies that recognize LOS determinants showed the typical "LOS" pattern in Western blot assays of whole cell preparations, in contrast to the well-defined single band recognized by antibody 7F3. Third, antibody 7F3 showed reactivity with cell envelope preparations that contain OMPs plus LOS (ELISA), but the antibody showed no reactivity with isolated LOS. Finally, in the Western blot assay (FIG. 4), antibody 7F3 recognized a band in whole cell preparation but failed to recognize determinants on LOS that was prepared by using two different methods. Taken together, these observations indicate that the epitope recognized by antibody 7F3 resides on an OMP.

To assess whether the OMP containing the antibody 7F3 epitope was surface exposed, OMPs were labeled by using the lactoperoxidase-catalyzed radioiodination procedure of Hansen et al, a3 described elsewhere herein. Referring again to FIG. 1, it is shown that the protein containing the antibody 7F3 epitope is radiolabeled. This observation suggests that this approximate 16,000 dalton OMP is surface e.,,posed. As used herein the term "surface exposed" or "outer membrane" means available for antibody binding.

The OMPs of nontypeable H. influenzas show substantial strain-to-strain variability, as demonstrated by SDS-PAGE analysis. This variability in the major OMPs in the 32,000 to 42,000 dalton range is the basis of the subtyping system for nontypeable H. influenzas as described by Murphy et al, J. Clin. Invest., 1986, 78:1020, the disclosure of which is hereby incoporated by reference. It is of interest that studies of OMPs of H. influenzas from other laboratories have independently noted the presence of a 16,600 dalton OMP in all strains of H. influenzas studied. It is this protein that contains the antigenic determinant recognized by antibody 7F3. The present study indicates that the epitope recognized by antibody 7F3 on this low molecular weight OMP is an antigen common to all strains of H. influenzas . Identifying common surface antigens amongst strains is useful from the point of view of vaccine development because immunization with a single common antigen could induce protection from disease due to a variety of strains. In addition, the observation that this 16,600 dalton protein has varied far less than other OMPs in the course of evolution leads to the speculation that this protein serves an important function for the bacterium and that its function is closely related to conservation of its structure.

The outer membranes of gram-negative bacteria are immunologically important structures because of their accessibility to host defense mechanisms. Antibodies to OMPs of H. influenzas type b are widely prevalent in adults and are detected in the serum of infants who are convalescing from infections with H. influenzas . The present invention has now demonstrated that antibody to a 16,600 dalton OMP (P6) is present in human serum. The presence of antibody to this OMP in normal human serum suggests that the OMP is important with regard to the human antibody response to H. influenzas . More significantly, several observations suggest that P6 is an important target in immunity to H. influenzas . First, antibody raised from P6 isolated from a type b strain protects in an infant rat model. Secondly, a monoclonal antibody, 7F3, directed against P6 blocks human bactericidal activity against H. influenzas. Thirdly, depleting normal human serum of antibodies to P6 by affinity chromatography resulted in reduced bactericidal activity of that sera for H. influenzas. Lastly, immunopurified antibody to P6 from human sera was bactericidal.

P6 may be cloned molecularly using H. influenzas as a source of bacterial chromosomal DNA. For example, bacteriophage lambda gt11 may be used as a vector in construction of the genomic library. Plasmid pUC18 may be used as the vector in subcloning the gene to facilitate sequencing and E. coli as the host strain. It is understood that the above cloning vehicles and host cell are illustrated for purposes of example only and not limitation. It is understood that any known cloning vector and compatible host for producing recombinant P6 may be substituted herein and still be within the scope of the present invention. Cloning P6 facilitates further analysis of the molecular basis of both experimental and human immunity to P6. Additionally, it permits large quantities of P6 to be produced once it is approved for use in vaccine against H. influenzas.

EXAMPLE IV

Molecular Cloning of P6

P6, a 16,600 dalton protein, is present in the outer membranes of both typeable and nontypeable strains of H. influenzas and may be an important target in immunity to the pathogen H. influenzas . The DNA sequence corresponding to the amino acid sequence of the approximate 16,000 dalton outer membrane protein P6 is believed to begin at nucleotide 125 and continue until nucleotide 526 (FIG. 11b). In one illustrative embodiment of the present invention, P6 may be cloned molecularly using a nontypeable strain of H. influenzas as a source of bacterial chromosomal DNA, lambda gt11 bacteriophage as the vector in construction of the genomic library, pUC18 plasmid as the vector in subcloning the gene to facilitate sequencing, and E. coli as the host strain. The monoclonal antibodies previously discussed and a polyclonal antiserum were used to screen for expression of P6. A portion of the genomic library was screened resulting in the detection of four positive recombinants. One such recombinant designated clone 0, appears to produce a full length gene product expressed in high frequency. The DNA insert of this clone was used to subclone the gene into a plasmid vector. An E. coli transformant, designated 7-9B, also appears to express a full length gene product. It is likely that transcription is initiated from the actual promoter of the P6 gene, since both clone 0 and transformant 7-9B express the gene product in both the uninduced and induced states.

Isolating and sequencing the gene for P6 allows for further analysis of the molecular basis of both experimental and human immunity to P6. Recombinant DNA technology was used to clone the gene for the 16,600 dalton surface protein, P6, of nontypeable H. influenzas (NtHi) into E. coli. Chromosomal DNA from a clinical isolate was sheared, ligated to bacteriophage lambda gt11 arms and packaged into phage heads. Four recombinant phages were detected by screening with monoclonal antibodies and a polyclonal antiserum. One such recombinant, clone 0, was restricted with EcoR1 and ligated to plasmid vector pUC18 to facilitate sequencing. E. coli carrying recombinant plasmids were screened resulting in one positive, designated 7-9B. Both clone 0 and transformant 7-9B produce a protein with an apparent molecular weight equal to or similar to native P6, as determined by Western blot analyses. In screening it was determined that transcription and translation of the H. influenzas P6 gene(s) were not dependent on the lac operator and promoter of either vector. Using immunofluorescence, the recombinant gene product's epitopes seem to be located on the surface of the E. coli host and thus made accessible to antibody.

H. influenzas strain 1479 was grown at 37° C. in brain heart infusion broth supplemented with heme (10 μg/ml)and nicotinamide adenine dinucleotide (10

μg/ml). *E. coli* strain y1090 (r−m+) was used for the lytic growth of bacteriophage lambda gt11 and strain JM83 as host for plamid pUC18. The *E. coli* strains were grown in L-broth (LB) or on LB agar with or without 50 μg/ml of ampicillin, depending on the host strain. A more detailed description for the use of the respective host strains is described by Young et al, *Science*, 222: 778-782, 1983; and Messing, *Rec. DNA Tech. Bull.*, 2:43-48, 1979, the disclosures of which are hereby incorporated by reference.

A pellet of *H. influenzas* 1479 cells from a 750 ml culture was resuspended in 10 mls of 10 mM HEPES buffer, pH 7.4. To this mi,-.lure was added EDTA to a concentration of 5 mM and SDS to a concentration of 0.5% w/v and then incubated at 60° C. for 30 minutes. This lysate was then digested with 0.5 ml of pronase (10mg/ml) at 37° C. for 2 hours and then subjected to two phenol/Chlorophorm isoamylalcohol 24:1 (CIMA) extractions followed by one CIAA extraction. Sodium chloride was added to a concentration of 0.2 M to the aqueous phase, and DNA was precipitated with 2.5 volumes of chilled ethanol. Following precipitation in the cold ethanol, the DNA was pelleted by centrifugation, resuspended in Tris-EDTA buffer, and treated with DNase-free RNase at a concentration of 0.1 mg/ml at 37° C. for 1 hour. The DNA was e,-,tracted with phenol/CIAA, precipitated with sodium chloride and ethanol, and pelleted by centrifugation. The DNA was resuspended in Tris-EDTA buffer, measured for concentration by $A_{260}/A_{280}$ and stored at 4° C.

The phage library was screened with monoclonal antibody 7F3. Also used in screening was rabbit polyclonal antiserum produced by immunizations with solubilized P6 preparations of *H. influenzas* strain 1808.

EXAMPLE V

Construction of the *H. influenzas* 1479 genomic library

Figure 6:
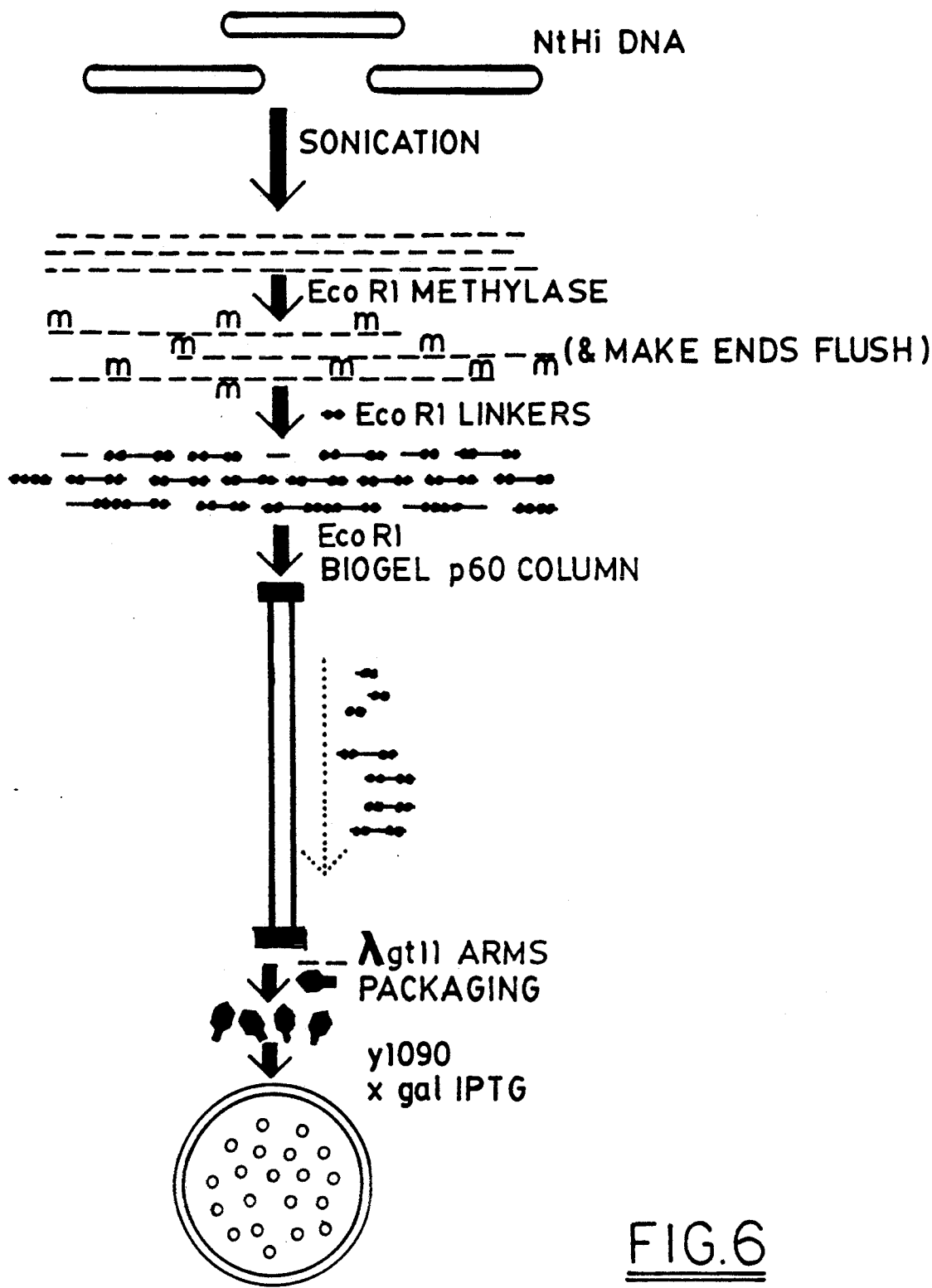
FIG. 6 illustrates the construction of the *H. influenzas* 1479 genomic library.

The methods for the construction of the library, as shown in FIG. 6, were essentially those described by Young et al, 1985, Vol. 7, pp 29-41, *Genetic Engineering*,Plenum Press, N.Y., the disclosure of which is hereby incorporated by reference. *H. influenzas* strain 1479 DNA was sheared by sonication with one 10 second burst (output control setting at 2) to an average length of 2-4 kilobase pairs (kb). The degree of shear was monitored by agarose gel electrophoresis. The EcoR1 sites of 50 μg of this sheared DNA were methylated using EcoR1 methylase. The ends of the methylated DNA were made flush by the addition of Klenow polymerase and deoxynucleotide triphosphates. Following this reaction and the addition of sodium acetate to a concentration of about 0.3 M, the DNA was precipitated. After centrifugation, the pellet was resuspended in Tris-EDTA buffer, The DNA was then ligated to EcoR1 linkers (Bethesda Research Laboratories, Bethesda, Md.) that had been phosphorylated. The ligation reaction was terminated by heating the mixture to 70° C. and then the excess EcoR1 linkers were digested using an excess of EcoR1. The methylated *H. influenzas* 1479 DNA blunt end-ligated to EcoR1 linkers was purified from excess linkers by passage over a gel filtration column (Biogel p60, BIO RAD laboratories, Richmond, Calif. A) using a column buffer containing 10 mM Tris, pH 7.5, 100 mM NaCl, 1 mM EDTA. Fractions were monitored by $A_{280}$ and agarose gel electrophoresis. Fractions containing DNA of desired size range were pooled and precipitated. The DNA was pelleted by centrifugation and resuspended in 4 μl of Tris-EDTA buffer. The DNA was ligated to 3 μg of dephosphorylated lambda gt11 arms (STRATAGENE TM Cloning Systems, San Diego, Calif.) in a total reaction volume of 10 μl. The ligation mixture was packaged using two packaging extracts according to the directions of the manufacturer (GIGAPACK TM, STRATAGENE TM Cloning Systems). Packaged phage were plated on *E. coli* strain y1090 to determine the titer of plaque forming units (pfus) and to determine the non-recombinant background by growth with IPTG and X-gal on LB+ AMP plates. The library contains approximately $1.5 \times 10^6$ independent recombinant clones with a background of less than or equal to 5.0%.

EXAMPLE VI

Screening the library

Figure 7:
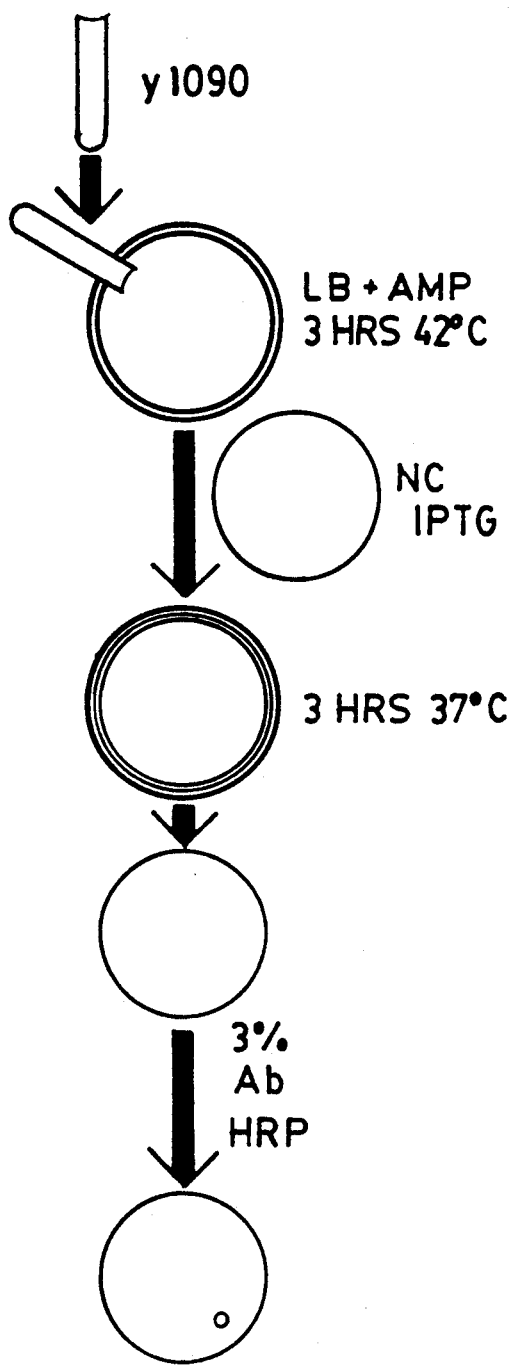
FIG. 7 illustrates the methods used in screening the library of FIG. 6.

With reference to FIG. 7, there is illustrated screening methods used in accordance with the present invention. A portion of the y1090 plating stock (0.2 ml of a y1090 pellet resuspended in 10 MM $MgSO_4$) was infected with $1.5 \times 10^3$ plaque forming units (pfus) of the lambda gt11 library for each 85 mm plate. Following adsorption incubation, cells were mixed with LB-agarose buffer, poured and spread evenly onto an LB+ AMP plate. The plates were incubated at 42° C. for 3 hours. Thereafter, each plate was overlaid with a dry nitrocellulose filter disk which had been saturated previously in 10 mM IPTG and incubated for 3 hours at 37° C. Before removing the filters, the orientation was marked and the filters and respective plates labeled. The filters were rinsed briefly with Buffer A (0.01 M Tris, 0.15 M NaCl, pH 7.4) and placed in 3% gelatin in Buffer A for 1 hour. After the filters were rinsed again with Buffer A, they were incubated in a screening mixture of antibodies overnight at 25° C. (room temperature). The screening mi-,lure was Buffer A containing 7F3 ascites fluid, at titers of 1:1000. The monoclonal antibody used shared no cross-reactivity with the *E. coli* host strains. The anti-1808 antiserum required a working dilution of 1:10,000 to maintain sensitivity and specificity. The filters were rinsed with Buffer A and placed in a 1:3000 dilution of protein A-peroxidase conjugate and shaken for 1 hour at 25° C. The filters were again rinsed with Buffer A, and then immersed in horseradish peroxidase color development solution (0.15% $H_2O_2$ BIO RAD, Richmond, Calif.) for 45 minutes. Plaques that appeared positive were removed from their respective plates, resuspended in 500 μls of SM buffer and rescreened. Plaques that were positive in the rescreening were then rescreened again but against the individual antibodies rather than the screening mixture.

EXAMPLE VII

Western blot analysis

The *H. influenzas* control, y1090 recombinants and molecular weight standards were prepared by heating at 100° C. for 5 minutes in a sample buffer containing 0.06 M Tris pH 6.8, 1.2% SDS, 5% beta-mercaptoethanol, 11.9% glycerol and 0.003% bromophenol blue. The preparations were subjected to SDS-PAGE on a 15% separating gel. Gels were placed on a nitrocellulose sheet which had been previously boiled in distilled water and immersed in a 0.3 M sodium citrate, 3 M NaCl solution. Electrophoretic transfer was done using a TransphorR electrophoresis unit (Hoefer Scientific Instruments, San Francisco, Calif.) at 50 volts for 90 minutes in a buffer of 0.025 M Tris, pH 8.3, 0.192 m glycine and 20% methanol. The blocking with subsequent additions of antibody, conjugate, and substrate development was performed in the same manner as described previously in the plaque screening example.

EXAMPLE VIII

Subcloning into a plasmed vector

A strategy was devised in accordance with the present invention to facilitate sequencing. The DNA insert (which consists of about 867 basepairs) of a recombinant phage e.-pressing P6 epitopes (as determined by screening) was subcloned into plasmid vector pUC18. pUC18 was chosen as the vector for subcloning because of its means of selection, inducible promotor EcoR1 restriction site and features shared with phage cloning vector lambda gt11. The DNA of a recombinant phage was restricted with EcoR1 and ligated to pUC18 which had been restricted with EcoR1 and dephosphorylated using calf intestinal alkaline phosphatase. The ligation mixture was used to transform competent E. coli strain JM83. Transformants were selected for by growth on LB+ AMP plates overlaid with IPTG and X-gal. White colonies, thought to represent JM83 containing a plasmid plus insert, were individually picked and transferred to wells of microtiter plates containing L-broth, AMP and 10% glycerol. The plates were incubated overnight at 37° C. A comb device was used to inoculate from the microtiter plates onto nitrocellulose sheets (previously immersed in IPTG) overlaying LB+ AMP plates. The plates were incubated overnight at 37° C., and then the nitrocellulose sheets were removed. The nitrocellulose was hung for 15 minutes in a chamber containing chloroform vapors to lyse the colonies, blocked in 3% gelatin containing 40 µg/ml lysozyme and screened in the same manner as the genomic library.

EXAMPLE IX

Screening the genomic library and characterization of recombinants

Approximately 45,000 plaques were screened, the remainder of the unamplified library being frozen in aliquots at −70° C. in 7% DMSO. Four reactive clones, designated as lambda gt11 H. influenzas 1479 clones 0, P, 8, and 10, were found. Further research was conducted on clones O and P since they appeared to express gene products that are in larger quantities than 8 or 10 and more closely resembled the conformation of the native protein, P6. Plates containing clones O and P were carefully scraped to harvest protein for Western blot analysis. Western blots show that both clones O and P produce a protein that is the same or similar in size to native P6. However, clone O produces the protein in larger quantities when compared to clone P. Therefore, clone O was selected as the recombinant phage for the source of DNA to subclone into a plasmid vector.

EXAMPLE X

Subcloning into a plasmed vector and characterization of the transformant 1000 transformants, from the same transformation, were screened before one, 7-9B, was found to be positive. To make certain that 7-9B was in pure culture, positive colonies were picked, passaged and rescreened. Western blots of 7-9B grown on plates, in broth, show that this recombinant also produces a gene product that is of an apparent molecular weight equal or similar to native P6. The recombinant plasmid isolated from 7-9B, was restricted using EcoR1 and subjected to agarose gel electrophoresis to determine insert size. Restriction analysis (not shown) reveals the presence of a 2.5 kb DNA insert containing the P6 gene.

Using molecular cloning techniques, both recombinant phages and recombinant plasmids containing the gene encoding for H. influenzas 1479 (P6), a 16.6 K-dalton outer membrane protein, was produced. The processed protein can be described as the amino acid sequence from about amino acid 20 to about amino acid 153, or by corresponding nucleic acid sequences between about nucleic acid 125 and about nucleic acid 526 inclusively. Expression of the gene product by phage clone 0 and by recombinant plasmid 7-9B is independent of induction of the beta-galactasidase promoter. This finding, coupled with Western blot analyses revealed apparently no difference in electrophoretic mobilities between the gene products of clone 0 and recombinant 7-9B. This is evidence for the likelihood that the recombinant gene product is initiated from its own (the P6 gene) constitutive promoter. The epitopes of the 16.6 K-dalton protein are accessible to monoclonal antibody 7F3 on the surface of E. coli transformant 7-9B.

All microbiological strains described herein are generally available, except as otherwise indicated, from Dr. Timothy Murphy, Division of Infectious Diseases, State University of New York Clinical Center, 462 Grider Street, Buffalo, N.Y. 14215. H. influenzas strains 3524 and 1479; E. coli transformant 7-9B, strain JM83 containing plasmid pBUD1 (originally designated 7-9B) and hybridoma 7F3 were deposited in accordance with the Budapest Treaty with the American Type Culture Collection (A.T.C.C.) at 12301 Parklawn Drive, Rockville, Md. 20852.

EXAMPLE XI

Purification of the Outer Membrane Protein of H. influenzas

Figure 2:
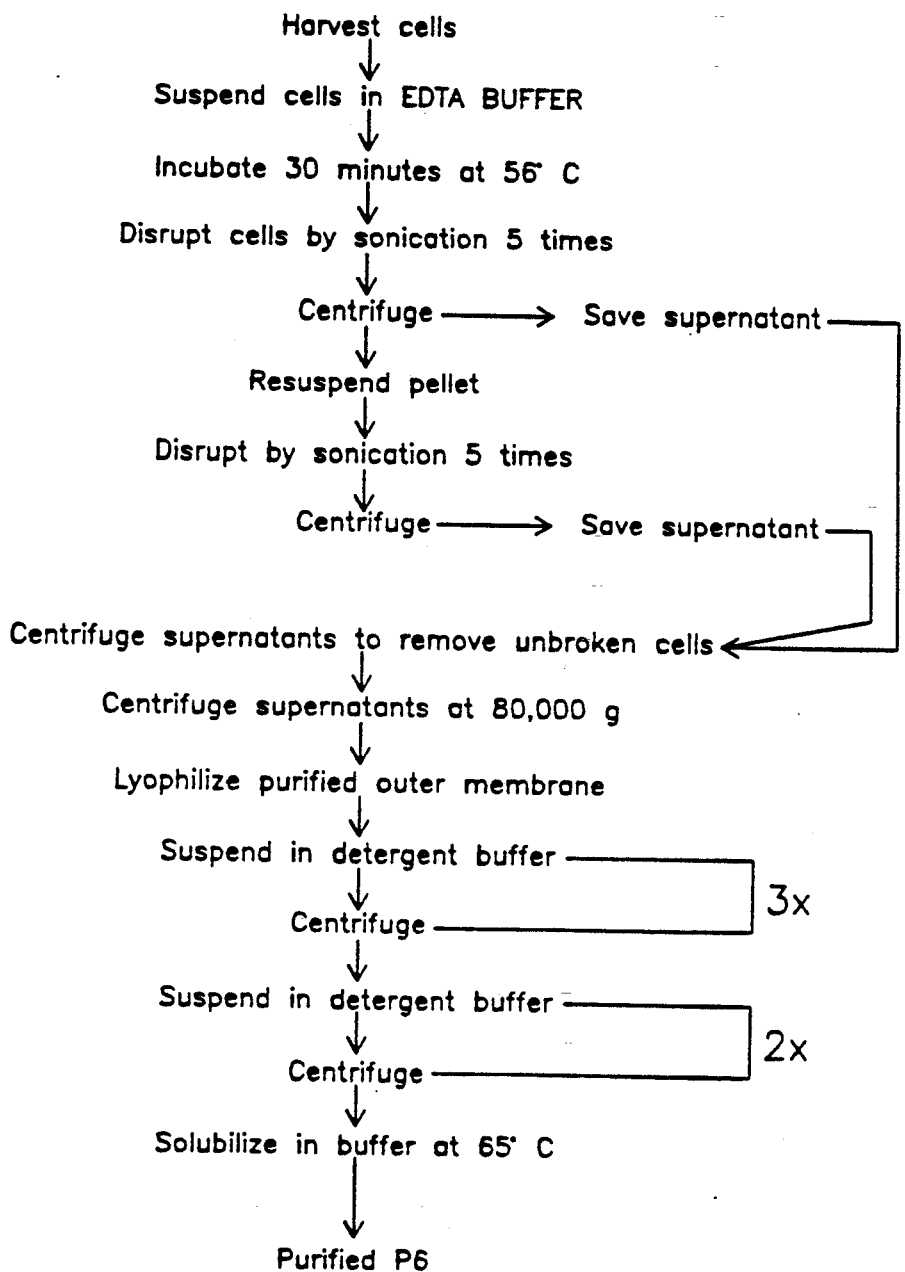

A method for purifying the outer membrane protein of H. influenzas is disclosed in accordance with the present invention. The purification method of the present invention is an unobvious improvement over the prior art method as disclosed in Murphy et al and shown in FIG. 2. The first series of steps in the purification of P6, as described in Murphy et al (FIG. 2), are directed to preparing an outer membrane complex comprising of outer membrane proteins and lipo-oligosaccharides. The outer membrane complex,-. is prepared by sequential incubation of the bacteria in a detergent such as sarcosyl, and thereafter centrifugation to obtain a sarcosyl-insoluble fraction containing the outer membrane protein. This sarcosyl-insoluble fraction is then subjected to buffer B. The new and improved method of the present invention omits the initial steps of the prior art method for first preparing an outer membrane complex,-,. In the method of the present invention, the whole bacterium are treated directly with buffer B, the resultant insoluble fraction consisting predominantly of outer membrane protein and peptidoglycan. The term "whole bacterium" as used herein, means bacterium which is used in an unprocessed state. This is very significant because not only is the method of the present invention easier, but of commercial significance, the yield of outer membrane protein P6 using the present method is substantially increased over the yield produced according to the prior art method of Murphy et al. With reference to FIG. 10, the approximate yield of P6 obtained from about 25 g (wet weight) of bacterial cells using the method of the present invention (FIG. 8) is substantially greater than the yield obtained using the prior art method of Murphy et al (FIG. 2).

It would not have been obvious to one skilled in the art to omit the step of preparing outer membrane complex using sarcosyl detergent as disclosed in Murphy et al (FIG. 2) because there would have been no reason to expect that all other bacterial components not found in the outer membrane i.e., inner membrane and cellular components, are soluble in the detergent buffer. Additionally, the fact that omitting the step of preparing outer membrane complex prior to buffer B treatment resulted in a substantial increase of yield of outer membrane protein is an unexpected result.

Another significant improvement in purification of P6 according to the method of the present invention over the prior art method, as disclosed in Murphy et al, is that the prior art method teaches the use of a final buffer which contains a detergent such as SDS, and possibly residual sarcosyl. Thus, the purified preparation of P6 (using the prior art method) contains detergent such as SDS, and possibly residual sarcosyl, which limits its potential usefulness in subsequent applications. For e,-ample, one such potential use of P6 is as a component in vaccine preparation. The presence of sodium dodecyl sulfate (SDS), the detergent used in buffer B, is not allowed in vaccine formulations. A further example involves current efforts to epitope map determinants on P6 by generating corresponding peptides using various proteinases. SDS inhibits many enzymatic reactions, and therefore, a substantially detergent-free final product is necessary. The method of the present invention uses a detergent-free buffer, sodium tetraborate, pH 9.5, as the final buffer for suspending the outer membrane protein.

Figure 8:
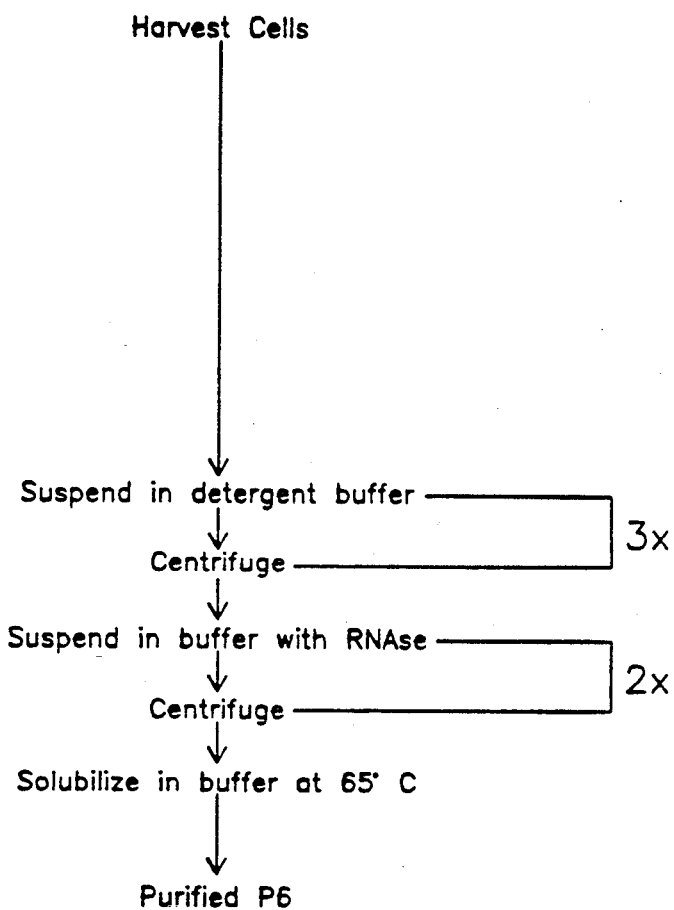
FIG. 8 is a flowchart illustrating the method of the present invention.

With reference to FIG. 8 $H.$ $influenzas$ (whole bacterium) are suspended directly in a suspending medium to form an insoluble fraction comprising the outer membrane protein and associated peptidoglycan component and a soluble fraction comprising the remainder of the cellular components. The suspending medium comprises a liquid in which the outer membrane protein and peptidoglycan component are insoluble and includes any suitable detergent buffer. For e.-ample, one suitable detergent may include sodium dodecyl sulfate (SDS). A suitable detergent buffer may include buffer B. Buffer B is comprised of 1% SDS, 0.1% betamercaptoethanol, 0.01 M tris, 0.5 M NaCl, pH 8.0. The insoluble fraction comprising the outer membrane protein and peptidoglycan component is obtained by successively heat treating and centrifuging the suspension. The suspension may be sonicated briefly to help suspend the cells. Heat treatment may be by any suitable means known to those skilled in the art. For example, heat treatment may comprise incubation at between about 20° C. to about 37° C. for about 20 to 40 minutes. Centrifugation may be carried out at about 20,000xg to about 40,000xg for about 30 to 60 minutes at ambient temperature. Ambient temperature, as used herein, means between about 20° C. to about 27° C. Successive heat treatment and centrifugation, as used herein, mean that the $H.$ $influenzas$ in the suspending medium, is heat treated then centrifuged then resuspended in the suspending medium and heat treated and centrifuged until an insoluble fraction in the form of a pellet comprising the outer membrane protein and peptidoglycan component is formed. The insoluble fraction (pellet) is then resuspended in the detergent buffer solution.

Contaminating RNA is then digested from the resuspended insoluble fraction by use of a digesting material in which the peptidoglycan and outer membrane protein remain insoluble and the digested contaminating RNA is soluble. Contaminating RNA is RNA which is present in the insoluble fraction along with the outer membrane protein and peptidoglycan. The digesting material allows for the digestion of contaminating RNA while the P6 remains in an insoluble form by virtue of its association with peptidoglycan. A suitable digesting material may comprise ribonuclease A (RNase). Once the digesting material is added to the detergent buffer solution which includes the insoluble fraction comprising the outer membrane protein and peptidoglycan component, the mixture is sequentially heat treated and centrifuged as described above. Then, the RNase and digested RNA which will be contained in the soluble fraction is separated from the insoluble fraction containing the outer membrane protein and peptidoglycan component. The outer membrane protein (P6) is then separated from the peptidoglycan component by solubilizing the insoluble fraction by heat-treating the fraction in a suitable solute in which the outer membrane protein is soluble and the peptidoglycan component is insoluble. A suitable solute within the scope of the present invention, in which the outer membrane protein is soluble and the peptidoglycan is insoluble, comprises a detergent-free buffer. A detergent-free buffer is a buffer solution which has no detergent added. For purposes of e.-.ample only and, not limitation, suitable detergent-free buffers include Tris, PBS and sodium tetraborate buffer solutions. The preferred detergent-free buffer solution is sodium tetraborate buffer. The insoluble fraction is solubilized by suspending the fraction in the detergent-free buffer and then heat-treating the solution at about 50° C. to about 75° C. for about 30 to about 60 minutes. The suspension is then centrifuged at about 80,000 xg to about 120,000 xg for a sufficient time of about 1 hour and at a sufficient temperature of about 37° C. until a supernatant comprising the outer membrane protein is obtained. The supernatant is then recovered which comprises a soluble preparation of P6 which is free of undesirable cellular components including lipooligosaccharides, proteins other than P6, peptidoglycan, DNA and RNA. The supernatant is then concentrated by any means known to those skilled in the art, such as pressure filtration. It is within the scope of the invention to remove any trace of detergent from the P6 preparation using columns of dialysis.

The following example describes the manner and process of making and using the invention and sets forth the best mode contemplated by the inventor at the time of the invention.

EXAMPLE XII 25 grams of bacteria grown up in broth were suspended in buffer B, sonicated briefly to help suspend the cells and incubated at 37° C. for 30 minutes. After incubation, the suspension was centrifuged at 20,000 xg for 30 minutes at 25° C. The supernatant was discarded and the insoluble fraction was resuspended in buffer B, incubated, and centrifuged as described above. The cycle of incubations and centrifugations was repeated a total of 5 times. For the last two incubations, 10 μg/ml of ribonuclease A was added to the buffer B solution. The ribonuclease allows for digestion of contaminating RNA while the P6 remains in an insoluble form by virtue of its association with peptidoglycan. The ribonuclease and RNA degradation products remain soluble. The P6/peptidoglycan insoluble fraction was resuspended in 0.1 M sodium tetraborate buffer, pH 9.5 and incubated for 30 minutes at 65° C. The mixture was then centrifuged at 100,000 Xg for 1 hour at 35° C. This step releases P6 from peptidoglycan whereby the solubilized P6 remains in the supernatant. The supernatant was then concentrated by pressure filtration approximately ten fold. The volume was brought back up to its original volume and reconcentrated. The concentrating and washing procedures were performed five times using the borate buffer.

Figure 9A:
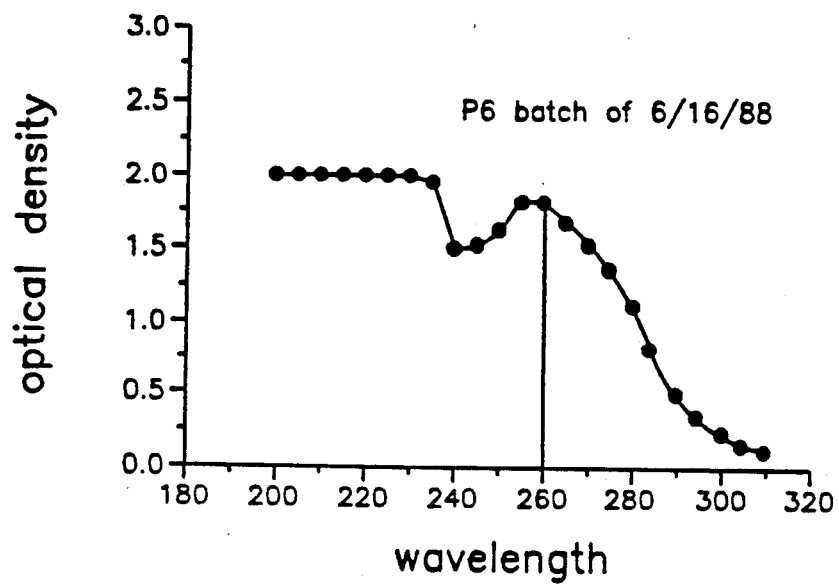
FIG. 9(a) is a graph showing the absorbance spectrum of a first batch purified P6.
Figure 9B:
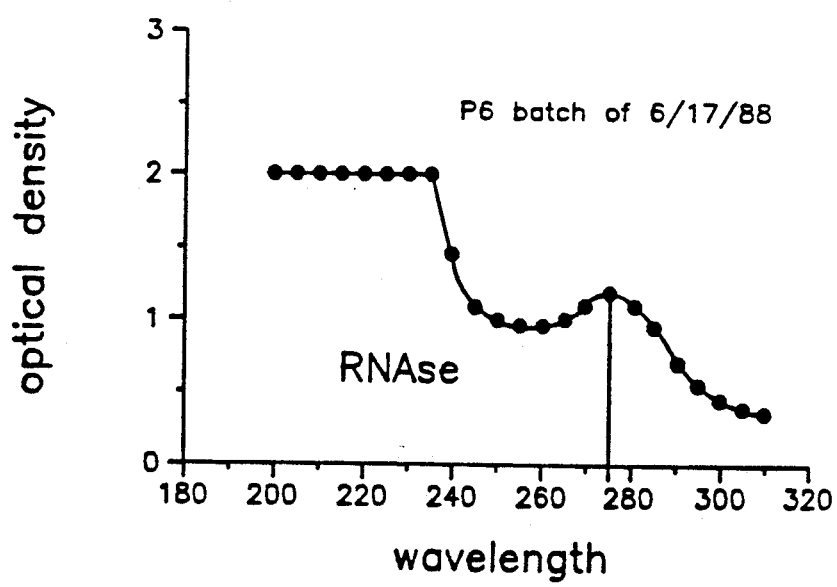
FIG. 9(b) is a graph showing the absorbance spectrum of a second batch purified P6.

The resulting P6 preparations were characterized. SDS-PAGE yielded a single protein band at a molecular weight of approximately 16,000 daltons. Using monoclonal antibody it was shown that the preparation was free of detectable lipo-oligosaccharide. With reference to Figures 9(a) and 9(b), absorbance spectrum of the soluble P6 (two different batches) revealed a peak at a wavelength of 260 nM and 275 nM. Agarose-gel electrophoresis revealed that the preparation was free of DNA and RNA. Therefore, the resulting preparations made in accordance with the method of the present invention contain purified, solubilized P6 protein from *H. influenzas*. Amino acid analysis of this material shows that the amino acid content is consistent with that predicted from the DNA sequence disclosed in the present invention.

It will be understood that the foregoing description and illustration is by way of example only and that such modifications and changes as may suggest themselves to those skilled in the art are intended to fall within the scope of the present invention as defined by the appended claims.

---

We claim:

1. A method for purifying an immunogenic outer membrane protein of *Haemophilus influenzas* consisting essentially of:
   a) suspending *H. influenzas* micro-organisms by incubating the organisms in a detergent buffer solution to form an insoluble fraction comprising the outer membrane protein and peptidoglycan component and a soluble fraction comprising the remainder of the cellular components;
   b) separating the insoluble fraction of step a) from the soluble fraction;
   c) suspending the insoluble fraction of step b) in detergent buffer containing RNase and allowing for RNA digestion;
   d) separating the insoluble fraction of step c) from the soluble fraction comprising the RNase and digested RNA;
   e) solubilizing the insoluble fraction of step d) by heat-treating in a detergent-free buffer; and
   f) separating the soluble fraction containing the purified outer membrane protein from the insoluble fraction of step e) containing the peptidoglycan component.

2. The method of claim 1, wherein the purified outer membrane protein is P6 having a molecular weight by SDS-PAGE under non-reducing conditions of from about 15,000 to about 17,000 daltons.

3. The method of claim 1, wherein said detergent buffer solution of step a) comprises an anionic detergent.

4. The method of claim 3, wherein said anionic detergent is sodium dodecyl sulfate.

5. The method of claim 4, wherein said buffer solution is buffer B comprising 1 wt. % sodium dodecyl sulfate, 0.01 M Tris, 0.5 M NaCl, 0.1% by volume beta-mercaptoethanol, pH 8.0.

6. The method of claim 1, wherein step a) further comprises sonication of the micro-organisms in the detergent buffer solution to facilitate suspension of the cellular components.

7. The method of claim 1, wherein said incubating of step a) is conducted by heat-treating the suspension at about 37° C. for about 30 minutes.

8. The method of claim 1, wherein the insoluble fraction is separated from the soluble fraction in step b) by centrifugation at about 100,000 xg for about 60 minutes, the insoluble fraction being in the form of a pellet.

9. The method of claim 8, further including the steps of:
   resuspending the insoluble fraction in a buffer solution; and
   repeating the heat treating of step a) and b) until the insoluble fraction is substantially free of soluble cellular components.

10. The method of claim 1, wherein said RNA digestion occurs by incubating the solution at about 37° C. for about 30 minutes.

11. The method of claim 1, wherein the Ribonuclease and digested RNA is separated out of the insoluble fraction in step d) by centrifugation.

12. The method of claim 1 wherein said detergent-free buffer comprises 0.1 M sodium tetraborate, pH 9.5.

13. The method of 1, wherein step f) further comprises:
   incubating the insoluble fraction at about 65° C. for about 30 minutes;
   immediately thereafter centrifuging the insoluble fraction at about 100,000 xg for about 1 hour at about 37° C.; and
   collecting the soluble fraction which contains the outer membrane protein.

14. The method of claim 13, wherein the soluble fraction is treated with pressure filtration to concentrate the outer membrane protein.

15. A method for purifying an outer membrane protein of *Haemophilus influenzae* consisting essentially of:
   a) suspending *H. influenzas* micro-organisms in a detergent buffer solution to form a suspension;
   b) heat-treating the suspension by incubating at about 37° C. for about 30 minutes to form a soluble and insoluble fraction;
   c) separating the insoluble fraction from the soluble fraction by centrifuging the suspension of step b) at about 100,000 xg for about 60 minutes at ambient temperature, the insoluble fraction being in the form of a pellet comprising the outer membrane protein and peptidoglycan component and the soluble fraction comprising the remainder of the cellular components;
   d) resuspending the pellet of step c) in a detergent buffer solution;
   e) repeating steps b) and c) until the insoluble fraction is substantially free of soluble cellular components;
   f) digesting RNA present in the insoluble fraction by adding ribonuclease A and incubating at about 37° C. for about 30 minutes;
   g) repeating step c) to remove the ribonuclease A which will be contained in the soluble fraction;
   h) solubilizing the insoluble fraction of step g) in a detergent-free buffer solution comprising 0.1 m sodium tetraborate, pH 9.5 by incubating at about 65° C. for about 30 minutes; and
   i) separating the outer membrane protein from the peptidoglycan component by centrifuging the solution of h) at about 100,000 xg, for about 1 hour at about 37° C., wherein the supernatant comprises the outer membrane protein.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 1019 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Haemophilus influenzae
        ( B ) STRAIN: 1479
        ( C ) INDIVIDUAL ISOLATE: 1479
        ( E ) HAPLOTYPE: N/A ( v i i ) IMMEDIATE SOURCE:
        ( A ) LIBRARY: N/A
        ( B ) CLONE: N/A ( v i i i ) POSITION IN GENOME:
        ( B ) MAP POSITION: Unknown ( x ) PUBLICATION INFORMATION:
        ( A ) AUTHORS: Nelson, M B
            Apicella, M A
            Murphy, T F
            VanKeulen, H
            Spotila, L D
            Rekosh, D M
        ( B ) TITLE: Molecular Analysis of P6: The cloning and
            sequencing of an Outer Membrane Protein
            Haemophilus Influenzae
        ( C ) JOURNAL: Infect. Immun.
        ( D ) VOLUME: 56
        ( F ) PAGES: 128-134
        ( G ) DATE: 1988

( x ) PUBLICATION INFORMATION:
        ( H ) DOCUMENT NUMBER: US 4,427,782
        ( I ) FILING DATE: 24-JAN-1984

( x ) PUBLICATION INFORMATION:
        ( H ) DOCUMENT NUMBER: US 4,474,758
        ( I ) FILING DATE: 02-OCT-1984

( x ) PUBLICATION INFORMATION:

(H) DOCUMENT NUMBER: US J.CLIN.INVEST.V.78
(J) PUBLICATION DATE: 01-OCT-1986
(K) RELEVANT RESIDUES IN SEQ ID NO:1: FROM 1020 TO 1027

(x) PUBLICATION INFORMATION:
(H) DOCUMENT NUMBER: US INFEC.IMMUN.V.49,N.3
(J) PUBLICATION DATE: 01-SEP-1985
(K) RELEVANT RESIDUES IN SEQ ID NO:1: FROM 544 TO 549

(xi) SEQUENCE DESCRIPTION: SEQ ID NO:1:

| | | | | | | |
|---|---|---|---|---|---|---|
| CACTTATATG | CTCACCTTAT | CAATACGAAA | ATAACTAGAC | CTCTACTAAC | TATAACATAC | 60 |
| AAACATATAC | AATATAATTC | GACGAATATA | CTTAATATCT | ATTATCCAAT | CATACTTATC | 120 |
| GTTTATGATA | TTTTATACTA | CGTGTGGTAC | CCCCCAAGTA | AAATTTCCAG | CTTGGTCTCC | 180 |
| ATACTTAACT | AAATAAAAAA | CTCATTTAGG | AGAAATCTAA | TGAACAAATT | TGTTAAATCA | 240 |
| TTATTAGTTG | CAGGTTCTGT | AGCTGCATTA | GCGGCTTGTA | GTTCCTCTAA | CAACGATGCT | 300 |
| GCAGGCAATG | GTGCTGCTCA | AACTTTTGGC | GGATACTCTG | TTGCTGATCT | TCAACAACGT | 360 |
| TACAACACCG | TATATTTTGG | TTTTGATAAA | TACGACATCA | CCGGTGAATA | CGTTCAAATC | 420 |
| TTAGATGCGC | ACGCAGCATA | TTTAAATGCA | ACGCCAGCTG | CTAAAGTATT | AGTAGAAGGT | 480 |
| AATACTGATG | AACGTGGTAC | ACCAGAATAC | AACATCGCAT | TAGGACAACG | TCGTGCAGAT | 540 |
| GCAGTTAAAG | GTTATTTAGC | AGGTAAAGGT | GTTGATGCTG | GTAAATTAGG | CACAGTATCT | 600 |
| TACGGTGAAG | AAAAACCTGC | AGTATTAGGT | CACGATGAAG | CTGCATATTC | TAAAAACCGT | 660 |
| CGTGCAGTGT | TAGCGTACTA | ATTCTTGGTA | TTTCTAATAC | TTGAAAAACA | GGATCCATTT | 720 |
| TTATTGGAT | CCTGTTTTGT | TTTCATCGTT | TGTAATTTAA | CCAATTAGCT | TGAAAGAATG | 780 |
| AATTTATTCT | TTTGATTCTA | AAATAAATGC | GTTATCATTA | ACTCATCAAC | ACAGTGGGTC | 840 |
| GTTAGCTCAG | TCGGTAGAGC | AGCGGACTTT | TAATCCGTTG | GTCGAAGGTT | CGAATCCTTC | 900 |
| ACGACCCACC | ACTCTCTGAT | TTAATTGTCC | AGTTGGGTTG | TTAGCTCAGT | TGGTAGAGCA | 960 |
| GCGGACTCTT | AATTCGTCGG | TCGAGAGTTC | GAGCCTCTCA | CAACCTACCA | TTCTTACCG | 1019 |